United States Patent [19]

Homma et al.

[11] Patent Number: 5,248,694
[45] Date of Patent: Sep. 28, 1993

[54] PLANT DISEASE PREVENTING AGENTS

[75] Inventors: Yasuo Homma, Sakado; Yasuo Fujimoto, Tokyo, both of Japan

[73] Assignee: Rikagaku Kenkyusho, Wako, Japan

[21] Appl. No.: 841,502

[22] Filed: Feb. 26, 1992

[30] Foreign Application Priority Data

Sep. 6, 1991 [JP] Japan ................... 3-227283

[51] Int. Cl.$^5$ ............................ A01N 43/16
[52] U.S. Cl. ................................... 514/460
[58] Field of Search ........................ 514/460

[56] References Cited

U.S. PATENT DOCUMENTS 4,599,233  7/1986  Misato et al. ............. 424/127

OTHER PUBLICATIONS

Abstract of Preliminary Paper For The 1991 Meeting Of The Plant Disease Pathological Society of Japan, II-45, p. 115.

J. Chem. Soc. Perkin Trans. I, pp. 865–869, (1985) John F. Grove, "Metabolic Products Of 'Phomopsis Oblonga'. Part 2$^1$. Phomopsolide A and B, Tiglic Esters Of Two 6-Substituted 5, 6-Dihydro-5-Hydroxypyran-2-Ones".

Noshita et al, C. A. vol. 115; 49202Z (1991).
Claydon et al, C. A. vol. 103; 103:67970e (1985).
Grove, C. A. vol. 103 (1985) 103:84,665h.

*Primary Examiner*—Allen J. Robinson
*Attorney, Agent, or Firm*—Oblon, Spivak, McClelland, Maier & Neustadt

[57] ABSTRACT

A plant disease preventing agent which comprises as an effective ingredient at least one compound represented by the following formula (I) and a carrier:

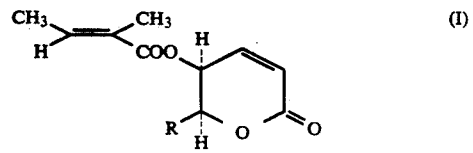

wherein R is selected from group consisting of 4-hydroxy-3-oxopent-1Z-enyl, 4 hydroxy-3-oxopent-1E-enyl, 3,4-dihydroxypent-1E-enyl and 1,4-dihydroxy-3-oxopentyl groups.

The agent is effective to prevent melanose spot disease of oranges, stem-end rot disease, grey mold of petunia petals and rice blight.

8 Claims, No Drawings

PLANT DISEASE PREVENTING AGENTS

BACKGROUND OF THE INVENTION

1. Field of the Invention

The present invention relates to a plant disease preventing agent which is not harmful to human, animals and plants.

2. Description of the Prior Art

Hitherto, there have widely been used such heavy metal compounds as cuprous agents, mercurials and arsenicals; organochlorine agricultural chemicals and organophosphorus agricultural chemicals as formulations of agricultural chemicals. However, all of these agricultural chemicals are not only harmful to human body and animals but also contaminate the soil. Therefore, the use of an effective amount of these chemicals leads to environmental pollution which is a serious social problem.

Under such circumstances, Japanese Patent Publication for Opposition Purpose (hereunder referred to as "J. P. KOKOKU") No. 57-48525 teaches that a fungicide mainly composed of an ester of an aliphatic polyol and an aliphatic acid and sodium hydrogen carbonate shows a prevention effect on various blight of plants and those observed during storing fruits and is highly safe with respect to human body, animals and plants.

However, the agricultural chemicals prepared according to such a method must be used in a high concentration in order to achieve a desired efficiency when they are used in an amount comparable to that of the conventional ones and on the contrary, if the concentration thereof is limited to a low level, a desired efficiency is attained only when they are used in a large amount.

SUMMARY OF THE INVENTION

Accordingly, an object of the present invention is to provide a plant disease preventing agent which is highly safe with respect to human body, animals and plants.

The inventors of this invention have done the study to elucidate the mechanism of the presentation of the symptoms of a plant disease and to prevent effectively the disease based on the finding. As a part of the study, they have investigated the mechanism of the presentation of the symptoms of melanose spot disease of oranges and stem-end rot disease. In the course of the study, they have found a substance in a culture solution of *Diaporthe citri*, which has the beta conidia inducing activity, i.e., which inhibits alpha conidial formation but induces beta conidial formation. They have accomplished the present invention based on this finding.

The present invention provides a plant disease preventing agent which comprises as an effective ingredient at least one compound represented by the following formula (I) and a carrier:

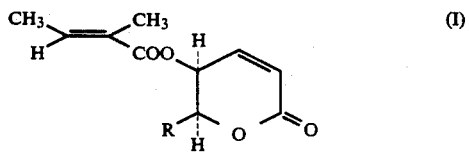

wherein R is selected from the group consisting of 4-hydroxy-3-oxopent-1Z-enyl, 4-hydroxy-3-oxopent-1E-enyl, 3,4-dihydroxypent-1E-enyl and 1,4-dihydroxy-3-oxopentyl groups. Specific examples of the compounds of the present invention are as follows:

(1) 5,6-dihydro-6-(4-hydroxy-3-oxopent-2Z-enyl)-5-(2-methylbut-2E-enoyloxy)-2H-pyran-2-one,
(2) 5,6-dihydro-6-(4-hydroxy-3-oxopent-1-oxopent-1E-enyl)-5-(2-methylbut-2E-enoyloxy)-2H-pyran-2-one,
(3) 5,6-dihydro-6-(3,4-dihydroxypent-1E-enyl)-5-(2-methylbut-2E-enoyloxy)-2H-pyran-2-one and
(4) 5,6-dihydro-6-(1,4-dihydroxy-3-oxopentyl)-5-(2-methylbut-2E-enoyloxy)-2H-pyran-2-one.

The compounds of the formula (I) which are used as an effective ingredient of the present invention have the beta conidia inducing activity, i.e., the activity to inhibit the formation of alpha conidia of the microorganisms belonging to *Diaporthe citri* which is a pathogen causing melanose spot disease of oranges and stem-end rot disease, Phomopsis and Phoma but to induce beta conidia thereof which are not pathogenic. Beta conidia once derived from alpha conidia never go back to alpha conidia. Therefore, when the plant disease preventing agent of the present invention is applied to petunia petals or rice plants, the degree of the disease such as grey mold of petunia petals and rice blast is reduced or eliminated and if it is previously applied to the plants, it is possible to prevent the outbreak of the plant diseases.

DETAILED EXPLANATION OF THE INVENTION

The compounds of the present invention are formulated using conventional solid carrier, liquid carrier, emulsifier or dispersing agent into any forms such as granule, powder, emulsion, wettable powder, tablet, oil, spray and smoke and applied to plants.

The carriers include such solid carrier as clay, kaolin, bentonite, acid clay, diatomaceous earth, calcium carbonate, nitorocellulose, starch, gum arabic, sodium alginate, carboxymethyl cellulose, and such liquid carrier as water, methanol, ethanol, acetone, dimethylformamide and ethyleneglycol. There may be incorporated conventional adjuvants such as sulfuric acid esters of higher alcohol, polyoxyethylene, alkyl allyl ether, alkyl allyl polyethylene glycol ether, alkyl allyl polyethylene glycol ether, alkyl allyl sorbitan monolaurate, alkyl allyl sulfonate, alkyl allyl sulfonic acid salt, quaternar ammonium salt, polyalkyleneoxide.

The compounds of the present invention may also be used in the form of coated formulations wherein the compounds are coated with one or more of aliphatic acid esters of aliphatic polyols or phospholipids.

As the aliphatic polyol moieties from which the aliphatic acid esters of aliphatic polyols used herein are produced, there may be employed saturated and unsaturated aliphatic polyols having 3 to 6 carbon atoms and preferred are glycerin, propylene glycol, sorbitol and sorbitan.

On the other hand, examples of the aliphatic acid moieties of the aliphatic acid esters of polyols herein used are individual aliphatic acids such as saturated aliphatic acids, for instance, caprylic acid, capric acid, lauric acid, myristic acid, palmitic acid, stearic acid, arachic acid and behenic acid; or unsaturated aliphatic acids, for instance, oleic acid, linolic acid, linolenic acid and ricinoleic acid; mixed aliphatic acids such as those naturally derived from animals or plants, for instance, tallow, cotton seed oil, rapeseed oil and hardened oil.

Examples of the aliphatic acid esters of the aliphatic polyols are mono-, di- or triesters prepared by esterifying the foregoing aliphatic polyols with the aliphatic acids or ester-interchanging in a conventional manner. In particular sorbitan monolaurate, sorbitan monostearate, glycerin monooleate, glycerin monooctoate, glycerin mono-soybean oil fatty acid ester, glycerin monocotton seed oil fatty acid ester, triglycerin monooleate, glycerin monopalmitate and polyglycerin fatty acid esters are preferably used.

Moreover, examples of the phospholipids used herein are phytolecithin derived from vegetable oils and egg yolk lecithin; and phosphatidylcholine, phosphatidylethanolamine and phosphatidylinositol separated therefrom.

The amount of the compound of the present invention (effective components) contained in the plant disease preventing agent of the present invention is suitably 10-90% by weight in emulsion and wettable powder and 0.1-90% by weight in powder and oil. The amount of the compound of the present invention (effective components) contained in the coated formulation is suitably 100 parts by weight per 0.1-10 parts by weight of the aliphatic acid esters of the aliphatic polyols or the phospholipids. The coated formulation is usually dispersed in water in the amount of 10~80% by weight based on the total weight of the dispersion and applied to plants.

The amount of the agent of the present invention applied to plants depends on the state of disease but typically is about 200 liters, if the concentration of the effective ingredient is in the range of about 1 to 1,000 ppm, per ten ares. The time when the agent be applied to is not critical but preferably before or after the infection.

The agent of the present invention may further comprise auxiliary agents commonly incorporated in compositions of agricultural chemicals such as surfactants, for instance, spreading agents, wetting and spreading agents and sticking agents according to need.

The agents of the present invention will hereunder be explained more specifically with reference to Examples, but the invention is not restricted to these specific Examples. Moreover, the effects practically attained by the present invention will also be discussed below in comparison with Comparative Examples.

Example 1 Wettable powder

Compound (1) (10 g), sodium laurylsulfate (5 g), sodium dioctylmethane disulfonate-formalin condensate (2 g) and clay (83 g) were mixed and pulverized to obtain wettable powder (100 g).

Example 2 Emulsion

Compound (2) (8 g), ethylene glycol (10 g), dimethylformamide (20 g), alkyl dimethylbenzyl ammonium chloride (10 g) and methanol (52 g) were mixed and dissolved to obtain an emulsion (100 g).

Example 3 Powder

Compound (3) (0.2 g), calcium stearate (0.5 g), talc (50 g) and clay (49.3 g) were mixed and pulverized to obtain powder (100 g).

Example 4 Coated formulation

Glycerin monooleate (2 g) was dissolved in 100 cc of acetone. Compound (2) (80 g), 90% of which passed through a sieve of 100 mesh, was added to the solution, followed by sufficiently stirring the mixture and completely distilling off the solvent utilizing a rotary evaporator to obtain powder. To the powder there was added 10 g of powdery sodium case in and the ingredients were admixed to form wettable powder having good flowability.

Example 5 Coated formulation

Diglycerin laurate (1 g) was dissolved in 100 cc of methanol. Compound (4) (80 g), 90% of which passed through a sieve of 300 mesh, was added to the solution, followed by sufficiently stirring the mixture and completely distilling off the solvent utilizing a rotary evaporator to obtain powder. To the powder there was added 10 g of powdery sodium case in and the ingredients were admixed to form wettable powder having good flowability.

Example 6 Preparation of Compounds (1) to (4)

*Diaporthe citri* obtained from Okitsu branch of the Horticultural Experimental Station of Ministry of Agriculture, Forestry and Fisheries (the method for the isolation is disclosed in Honma and Yamada, The Horticultural Experimental Station Report, B,No. 9, pp.99-115) was inoculated to a liquid medium (YSS) consisting of yeast extract (2 g), starch (10 g), sucrose (40 g) and water (1,000 g) and cultured with shaking at 25° C., for seven weeks. The culture solution was filtered and the filtrate was charged on an ion-exchange resin column (Diaion HP) and eluted with a water-methanol mixed solvent. The fractions eluted by water-methanol (20:80) and methanol were collected and subjected to high performance liquid chromatography (Column: Senshu pack, ODS-5251-SS (250×30 mm, i.d.), Mobile phase: (A) $H_2O$, (B) $CH_3CN$, Gradient elution: $CH_3CN$ 35-100%/30 min., Flow rate: 14 ml/min., Charged amount: 150 mg/800 µl, Detection: Uv 254 nm) to obtain Compounds (1), (2), (3) and (4) in the amounts of 571 mg, 432 mg. 784 mg and 123 mg. respectively.

IR, MASS and NMR analysis of the compounds showed that they have the chemical structure of the above mentioned formula (I) Compounds (1), (2) and (3) are known (J. F. Grove, J. Chem. Soc. Perkin Trans. I, 865 (1985)) but Compound (4) is novel and has the following physicochemical properties.

Compound (4)

CI-MS: m/z 313.1273 $(M+H)^+$, $C_{15}H_{20}O_7$ $^1$NMR (400 MHz, $CDCl_3$), δ: 1.37(3 H, d, J=7.0 Hz, H-11), 1.81(3 H, d, J=6.6 Hz, H-4'), 1.83(3 H, brs, H-5'), 2.78(2 H, d, J=4.8 Hz, H-8), 4.26(1 H, q, J=7.0 Hz, H-10), 4.52(1 H, dt, J=4.8, 7.0 Hz, H-7), 4.59(1 H, dd, J=2.9, 7.0 Hz, H-6), 5.45(1 H, dd, J=2.9, 5.9 Hz, H-5), 6.23(1 H, d, J=9.5 Hz, H-3), 6.91(1 H, brq, J=6.6 Hz, H-3'), 7.05(1 H, dd, J=5.9, 9.5 Hz, H-4)

$^{13}$ C-NMR (100 MHz, $CDCl_3$),δ: 12.0(C-5'), 14.6(C-4'), 19.1(C-11),39. 3(C-8), 61.6(C-5), 66.9(C-7), 73.6(C-10), 80.5(C-6), 125.2(C-3), 127.3(C-2'), 140.4(C-3'), 140.7(C-4), 162.2(C-2), 166.6(C-1'), 211. 1(C-9)

Test Example 1

A spray of oranges (2 cm in length and 0.5 cm in diameter) was placed in a test tube. water (500µl) was added and sterilized. *Diaporthe citri* was inoculated and cultured at 25° C. for 21 days while shading the light in an incubator. The compound was added in a given concentration. The test tube was placed under natural light and the cultivation was conducted at 25° C. for 20 days to induce pycnospore formation. The pycnospores formed was sufficiently dispersed in 5 ml of distilled water. The dispersion were observed under an optical microscope (×200) and the number of alpha conidia and beta coidia was counted to calculate a ratio of beta conidia induced to all conidia formed. The results are shown in Table 1.

TABLE 1

| | Beta conidial formation in *Diaporthe citri* | |
|---|---|---|
| Compound | Concentration | A ratio of beta conidia induced (%) |
| (1) | 3.0 mg/300 μl | 10 |
| (2) | 3.0 mg/300 μl | 60 |
| (3) | 6.0 mg/300 μl | 17 |
| (4) | 3.0 mg/300 μl | 55 |
| Control | 0.0 | 1 |

Test Example 2

Spores of pathogenic fungi which cause grey mold of petunia petals were cultured in a potato soup agar plate medium at 25° C. for 10 days and collected with water. One drop of Tween 20 was added to the collected spores to make the spreading better.

Petals of petunia were treated with the compound in a given concentration and dried. On the treated petals of petunia, the spores were sprayed. The petals were maintained for 24 hours without being dried. The number of disease spots was counted to calculate the inhibition ratio of the disease. The results are shown in Table 2.

TABLE 2

| Inhibition of grey mold disease of petunia petals | | |
|---|---|---|
| Compound | Concentration (ppm) | Inhibition ratio (%) |
| (1) | 200 | 93 |
| (2) | 200 | 95 |
| (3) | 200 | 90 |
| (4) | 200 | 100 |
| Control | 0 | 0 |

Test Example 3

In the same manner as in Test Example 2, spores of pathogenic fungus which cause rice blast were cultured and collected with water. One drop of Tween 20 was added to the collected spores to make the spreading better.

Spores of pathogenic fungus which cause rice blast were treated with the compound in a given concentration. After four days, the degree of inhibition of germination was observed and the germination inhibition ratio was calculated. The results are shown in Table 3.

TABLE 3

| Inhibition of germination of spores of rice blast pathogen | | |
|---|---|---|
| Compound | Concentration (ppm) | Inhibition of germination (%) |
| (1) | 100 | 10 |
| (2) | 100 | 100 |
| (3) | 100 | 71 |
| (4) | 100 | 94 |
| Control | 0 | 0 |

What is claimed is:

1. A method of treating a plant disease selected from the group consisting of
   (a) a plant disease caused by a microorganism belonging to Diaporthe, Phomopsis or Phoma;
   (b) grey mold; and
   (c) rice blast which comprises:

providing a plant disease treating composition comprising an effective amount of at least one compound represented by the following formula (I) and a carrier

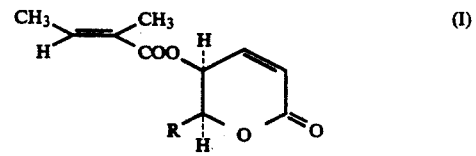

wherein R is selected from the group consisting of 4-hydroxy-3-oxopent-1Z-enyl, 4-hydroxy-3-oxopent-1E-enyl, 3,4-dihydroxypent-1E-enyl and 1,4-dihydroxy-3-oxopentyl groups; and applying said composition to said microorganism causing said plant disease, wherein said composition is applied to the microorganism in the form of a solution or dispersion containing from about 1 to 1000 ppm of the compound of formula (I), in the amount of about 200 liters per 10 ares.

2. The method of treating a plant disease of claim 1 wherein the compound is 5,6-dihydro-6-(4-hydroxy-3-oxopent-1Z-enyl)-5-(2-methylbut-2E-enoyloxy)-2H-pyran-2-one.

3. The method of treating a plant disease of claim 1 wherein the compound is 5,6-dihydro-6(4-hydroxy-3-oxopent-1E-enyl)-5-(2-methylbut-2E-enoyloxy)-2H-pyran-2-one.

4. The method of treating a plant disease of claim 1 wherein the compound is 5,6-dihydro-6-(3,4-dihydroxypent-1E-enyl)-5-(2methylbut-2E-enoyloxy)-2H-pyran-2-one.

5. The method of treating a plant disease of claim 1 wherein the compound is 5,6-dihydro-6-(1,4-dihydroxy-3-oxopentyl)-5-(2-methylbut-2E-enoyloxy)-2H-pyran-2-one.

6. The method of treating a plant disease of claim 1 wherein the disease is melanose spot disease of oranges, stem-end rot disease, grey mold of petunia petals or rice blast.

7. A method of treating a plant disease selected from the group consisting of
   (a) a plant disease caused by a microorganism belonging to Diaporthe, Phomopsis or Phoma;
   (b) grey mold; and
   (c) rice blast which comprises:

providing a plant disease treating composition comprising an effective amount of at least one compound represented by the following formula (I) and a carrier

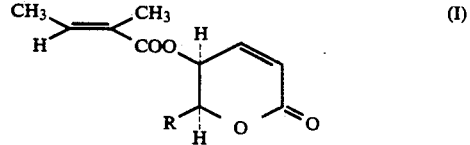

wherein R is selected from the group consisting of 4-hydroxy-3-oxopent-1Z-enyl, 4-hydroxy-3-oxopent-1E-enyl, 3,4-dihydroxypent-1E-enyl and 1,4-dihydroxy-3-oxopentyl groups; and applying said composition to said microorganism causing said plant disease, wherein sad composition is applied to the microorganism int he form of a granule, powder, emulsion, wettable powder, tablet, oil, spray or smoke containing from about 1 to 1000 ppm of the compound of formula (I) in the amount of about 200 liters per 10 ares.

8. A method of treating a plant disease selected from the group consisting of
   (a) a plant disease caused by a microorganism belonging to Diaporthe, Phomopsis or Phoma;
   (b) grey mold; and
   (c) rice blast
which comprises:
providing a plant disease treating composition comprising an effective amount of at least one compound represented by the following formula (I) and a carrier $$\text{(I)}$$

wherein R is selected from the group consisting of 4-hydroxy-3-oxopent-1Z-enyl, 4-hydroxy-3-oxopent-1E-enyl, 3,4-dihydroxypent-1E-enyl and 1,4-dihydroxy-3-oxopentyl groups; and applying said composition to said microorganism causing said plant disease, wherein said composition is applied to the microorganism in the form of a coated formulation wherein 100 parts by weight of the compound is coated with 0.1–10 parts by weight of one or more aliphatic acid esters of aliphatic polyols or phospo lipids, wherein said coated formulation contains from about 1 to 1000 ppm of the compound of formula (I) in the amount of about 200 liters per 10 ares.

* * * * *